US008295635B2

(12) United States Patent
McBeth et al.

(10) Patent No.: US 8,295,635 B2
(45) Date of Patent: Oct. 23, 2012

(54) METHODS AND APPARATUS FOR FACILITATING ELIMINATION OF AMBIENT LIGHT FROM AN IMAGE

(75) Inventors: Jeffrey B. McBeth, Rochester, NY (US); Lloyd G. Allred, Rochester, NY (US); Ning Zhang, Penfield, NY (US); Barry T. Eagan, Spencerport, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 990 days.

(21) Appl. No.: 12/266,026

(22) Filed: Nov. 6, 2008

(65) Prior Publication Data
US 2010/0111381 A1    May 6, 2010

(51) Int. Cl.
*G06K 9/40* (2006.01)
(52) U.S. Cl. ........................................ 382/274
(58) Field of Classification Search ............... 382/274
See application file for complete search history.

(56) References Cited

U.S. PATENT DOCUMENTS

| | | | | |
|---|---|---|---|---|
| 4,416,536 | A * | 11/1983 | Itoh et al. | 399/128 |
| 5,512,965 | A | 4/1996 | Snook | |
| 5,512,966 | A | 4/1996 | Snook | |
| 5,631,976 | A * | 5/1997 | Bolle et al. | 382/174 |
| 6,021,210 | A * | 2/2000 | Camus et al. | 382/117 |
| 6,286,958 | B1 | 9/2001 | Koest | |
| 6,575,573 | B2 | 6/2003 | Lai | |
| 6,692,126 | B1 | 2/2004 | Xie | |
| 7,102,740 | B2 * | 9/2006 | Clark et al. | 356/237.1 |
| 7,119,889 | B2 * | 10/2006 | Carver et al. | 356/71 |
| 2002/0113882 | A1 * | 8/2002 | Pollard et al. | 348/239 |
| 2003/0015645 | A1 * | 1/2003 | Brickell et al. | 250/208.1 |
| 2005/0243175 | A1 * | 11/2005 | Yamada et al. | 348/207.1 |
| 2006/0033835 | A1 * | 2/2006 | Pollard et al. | 348/370 |
| 2006/0135224 | A1 * | 6/2006 | Patino et al. | 455/575.3 |
| 2007/0188709 | A1 | 8/2007 | Saarloos | |
| 2008/0205701 | A1 * | 8/2008 | Shamaie et al. | 382/103 |
| 2008/0231564 | A1 * | 9/2008 | Harada et al. | 345/81 |
| 2008/0267600 | A1 * | 10/2008 | Omi | 396/14 |

OTHER PUBLICATIONS

U.S. Appl. No. 12/264,965, filed Nov. 5, 2008, Allred.

* cited by examiner

*Primary Examiner* — David Zarka
(74) *Attorney, Agent, or Firm* — Jeffrey B. Powers (57) ABSTRACT

An apparatus for facilitating elimination of ambient light from an image of an object, comprising an illumination apparatus adapted to sequentially illuminate the object using multiple lighting arrangements, an image sensor. The apparatus adapted to form on the image sensor (i) a first image of the object using a first illumination arrangement, (ii) a second image of the object using a second illumination arrangement, and (iii) a dark image of the object without illumination. The image sensor is adapted to A) compare an intensity value of a first pixel in the first image to an intensity value of a corresponding, first pixel in the second image to determine a first minimum intensity value, B) determine if the first minimum intensity value is greater than an intensity value of a corresponding, first pixel in the dark image by greater than a predetermined amount; and C) identify an ambient intensity value (a) as the first minimum intensity value, if the first minimum intensity value is not greater than the intensity value of the first pixel in the dark image by greater than the predetermined amount, or (b) as the intensity value of the first pixel in the dark image, if the first minimum intensity value is greater than the intensity value of the first pixel in the dark image by greater than the predetermined amount.

18 Claims, 6 Drawing Sheets

METHODS AND APPARATUS FOR FACILITATING ELIMINATION OF AMBIENT LIGHT FROM AN IMAGE

FIELD OF INVENTION

The present invention relates to methods and apparatus for measuring an object by imaging the object using multiple lighting arrangements, and more particularly to methods and apparatus for measuring an object by imaging the object using multiple lighting arrangements wherein the methods and apparatus reduce the impact of ambient light.

BACKGROUND OF THE INVENTION

Ophthalmologists and optometrists would like to have an accurate representation of subjects' eyes. Such representations include, for example, one or more of a representation of a subject's corneal anterior surface, posterior surface, and corneal thickness and density, as well as anterior chamber profiles. This information may be used to prescribe contact lenses and eye glasses, and to reshape the cornea by surgical procedures or to perform other surgical procedures. Since it is not comfortable to measure these data with physical contact, remote sensing techniques are preferably used to perform the measurements.

One common technique for obtaining eye measurement information includes projecting narrow bands of light (commonly referred to as slits or slit beams) onto a patient's eye at multiple locations across the cornea using a slit projector and for each slit imaging a cross section of the eye. A slit projector typically includes an aperture of appropriate shape and size, and a lens placed in the path of light from a light source such that the light passing through the aperture forms a long narrow pattern of light on the subject's cornea.

Typically, to project slits at each of multiple locations across the cornea, a portion of the slit projector is moved such that the light passing through the aperture at selected times forms the multiple slits. One example of such an eye measurement apparatus, in which a portion of the slit projector is translated, is presented in U.S. Pat. No. 5,512,966 to Snook. In another embodiment, a portion of the slit projector may be rotated as described in U.S. Pat. No. 6,286,958 by Koest. In another embodiment, multiple projectors may be arranged to project slits at multiple locations on the cornea as in United States Patent Appl. No. 2007/0188709 by Van Saarloos.

In the embodiments described above, for each of the slits, after the light in the slit has been scattered by the eye, an image of a cross section of the eye is obtained. A problem with such apparatus is that, in addition to the scattered light from the slits of light, the cross sectional images typically include ambient light from sources other that the slit projectors (e.g. room lights)).

SUMMARY

Aspects of the present invention are directed to a method of reducing the amount of light that is present in images which originates from one or more light sources other than light from projected slits. Such other light sources include, for example, room lighting or illumination from an eye tracker of an eye measurement apparatus that includes the slit apparatus. Light from sources other than the slits is referred to herein as ambient light. According to aspects of the present invention, ambient light is identified, and reduced or eliminated.

To reduce the ambient light, a first image of an object is obtained using a first slit illumination arrangement (e.g., light from a first slit location is projected onto an eye), a second image of the object is obtained using a second slit illumination arrangement (e.g., light from a second slit location is projected onto the eye), and a dark image of the object is obtained without slit illumination (e.g., the slit lamps are turned off during acquisition of the dark image). A portion (e.g., a pixel) of the first image and a corresponding portion (e.g., a pixel) of the second image that each includes the same features of the eye are compared. The minimum of the intensity value of the portion in the first image and the intensity value of the corresponding portion in second image is assumed to be indicative of the amount of ambient light present in the images at said portions.

In some instances, at a portion at which a comparison takes place, one or more of the images may include an image of a feature of the eye (e.g., the cornea) that is illuminated by the slit. If the portion is illuminated by the slit is only one image, the apparatus will accurately identify the minimum value as an indication of the amount of ambient light present at that portion. However, if in both images the portion is illuminated by slit light, the minimum will not be indicative of the ambient illumination. Accordingly, according to aspects of the present invention, after a minimum value is determined for the particular portions of the images, the minimum is compared to a corresponding portion of the dark image. If the minimum intensity value is greater than the intensity value of the portion in the dark image by greater than a predetermined amount, it is assumed that the minimum also correspond to an image of a feature of the eye that is illuminated by a slit, and the amount of ambient light present at the portion is taken as the amount present in the corresponding portion of the dark image.

For example, first and second illumination arrangements can be achieved by selectively positioning a slit mask as in the apparatus of U.S. Pat. No. 5,512,966 to Snook. Alternatively, a first and a second illumination arrangement can be achieved by rotating a mask as described in U.S. Pat. No. 6,286,958 by Koest. In yet another embodiment, first and a second illumination arrangements can be achieved by selectively illuminating multiple slit projectors as described in United States Patent Appl. No. 2007/0188709 by Van Saarloos. The subject matter of said, three patent filings is hereby incorporated by reference.

An aspect of the invention is directed to a method of facilitating elimination of ambient light from an image, comprising A) obtaining a first image of an object using a first illumination arrangement; B) obtaining a second image of the object using a second illumination arrangement; C) obtaining a dark image without illumination; D) comparing an intensity value of a first pixel in the first image to an intensity value of a corresponding, first pixel in the second image to determine a first minimum intensity value; E) determining if the first minimum intensity value is greater than an intensity value of a corresponding, first pixel in the dark image by greater than a predetermined amount; and F) identifying an ambient intensity value (a) as the first minimum intensity value, if the first minimum intensity value is not greater than the intensity value of the first pixel in the dark image by greater than the predetermined amount, or (b) as the intensity value of the first pixel in the dark image, if the first minimum intensity value is greater than the intensity value of the first pixel in the dark image by greater than the predetermined amount.

In some embodiments, the first illumination arrangement is achieved using a first slit arrangement and the second illumination arrangement is achieved using a second slit arrangement. In some embodiments, the first illumination arrangement and the second illumination arrangement are achieved by selectively illuminating multiple slit projectors. In some embodiments, the first illumination arrangement and the second illumination arrangement are achieved by selectively positioning one or more slit masks. In some embodiments, the selective positioning comprises at least one of translation and rotation of the one or more slit masks.

In some embodiments, the method further comprises subtracting an intensity value equal to the ambient intensity value from one or both of the first pixel in the first image and the first pixel in the second image. In some embodiments, the first image and the second image constitute two images of a plurality of images of an eye, and the method further comprises combining the plurality of images to produce a two-dimensional or a three-dimensional representation of the eye.

In some embodiments, the method further comprises a step of performing a perspective transform on at least one of the first image and the second image prior to step D).

In some embodiments, the method further comprises G) comparing an intensity value of a second pixel in the first image to an intensity value of a corresponding, second pixel in the second image to determine a second minimum intensity value; H) determining if the second minimum intensity value is greater than an intensity value of a corresponding, second pixel in the dark image by greater than a second predetermined amount; and I) identifying an ambient intensity value (a) as the second minimum intensity value, if the second minimum intensity value is not greater than the intensity value of the second pixel in the dark image by greater than the predetermined amount, or (b) as the intensity value of the second pixel in the dark image, if the second minimum intensity value is greater than the intensity value of the second pixel in the dark image by greater than a second predetermined amount.

Another aspect of the invention is directed to an apparatus for facilitating elimination of ambient light from an image of an object, comprising an illumination apparatus adapted to sequentially illuminate the object using a first lighting arrangement and a second lighting arrangement, an image sensor, and a processor. The apparatus is adapted to form on the image sensor (i) a first image of the object using the first illumination arrangement, (ii) a second image of the object using the second illumination arrangement, and (iii) a dark image of the object without illumination. The processor is coupled to the image sensor and is adapted to A) compare an intensity value of a first pixel in the first image to an intensity value of a corresponding, first pixel in the second image to determine a first minimum intensity value, B) determine if the first minimum intensity value is greater than an intensity value of a corresponding, first pixel in the dark image by greater than a predetermined amount; and C) identify an ambient intensity value (a) as the first minimum intensity value, if the first minimum intensity value is not greater than the intensity value of the first pixel in the dark image by greater than the predetermined amount, or (b) as the intensity value of the first pixel in the dark image, if the first minimum intensity value is greater than the intensity value of the first pixel in the dark image by greater than the predetermined amount.

In some embodiments, the illumination apparatus comprises one or more slit masks configured to achieve the first illumination arrangement and the second illumination arrangement. In some embodiments, the illumination apparatus comprises a plurality of slit projectors adapted to be selectively illuminated to achieve the first slit arrangement and the second slit arrangement. In some embodiments, the illumination apparatus comprises one or more slit projectors adapted to be selectively positioned to achieve the first slit arrangement and the second slit arrangement. The one or more slit projectors may be adapted to be translated to achieve the first slit arrangement and the second slit arrangement. The one or more slit projectors may be adapted to be rotated to achieve the first slit arrangement and the second slit arrangement.

In some embodiments, the processor is further adapted to subtract an intensity value equal to the ambient intensity value from one or both of the first pixel in the first image and the first pixel in the second image. In some embodiments, the apparatus is adapted to obtain a plurality of images of an eye, the first image and the second image constituting two images of the plurality of images, and wherein the processor is adapted to combine the plurality of images to produce a two-dimensional or a three-dimensional representation of the eye.

The processor may be adapted to perform a perspective transform on at least one of the first image and the second image prior to the comparing of the intensity value of the first pixel in the first image to the intensity value of the corresponding, first pixel in the second image to determine the first minimum intensity value.

In some embodiments, the processor is further adapted to E) compare an intensity value of a second pixel in the first image to an intensity value of a corresponding, second pixel in the second image to determine a second minimum intensity value, F) determine if the second minimum intensity value is greater than an intensity value of a corresponding, second pixel in the dark image by greater than a second predetermined amount; and G) identify an ambient intensity value (a) as the second minimum intensity value, if the second minimum intensity value is not greater than the intensity value of the second pixel in the dark image by greater than the second predetermined amount, or (b) as the intensity value of the second pixel in the dark image, if the second minimum intensity value is greater than the intensity value of the second pixel in the dark image by greater than the second predetermined amount.

The processor may be adapted to interpolate data (e.g., intensity values) in the first image prior to comparison of an intensity value of the pixel in the first image to the intensity value of the corresponding, first pixel in the second image to determine the first minimum intensity value. The image sensor may be an interlaced image sensor, the first image and the second image constituting interlaced images.

BRIEF DESCRIPTION OF THE DRAWINGS

Illustrative, non-limiting embodiments of the present invention will be described by way of example with reference to the accompanying drawings, in which the same reference number is used to designate the same or similar components in different figures, and in which.

DETAILED DESCRIPTION

Figure 1:
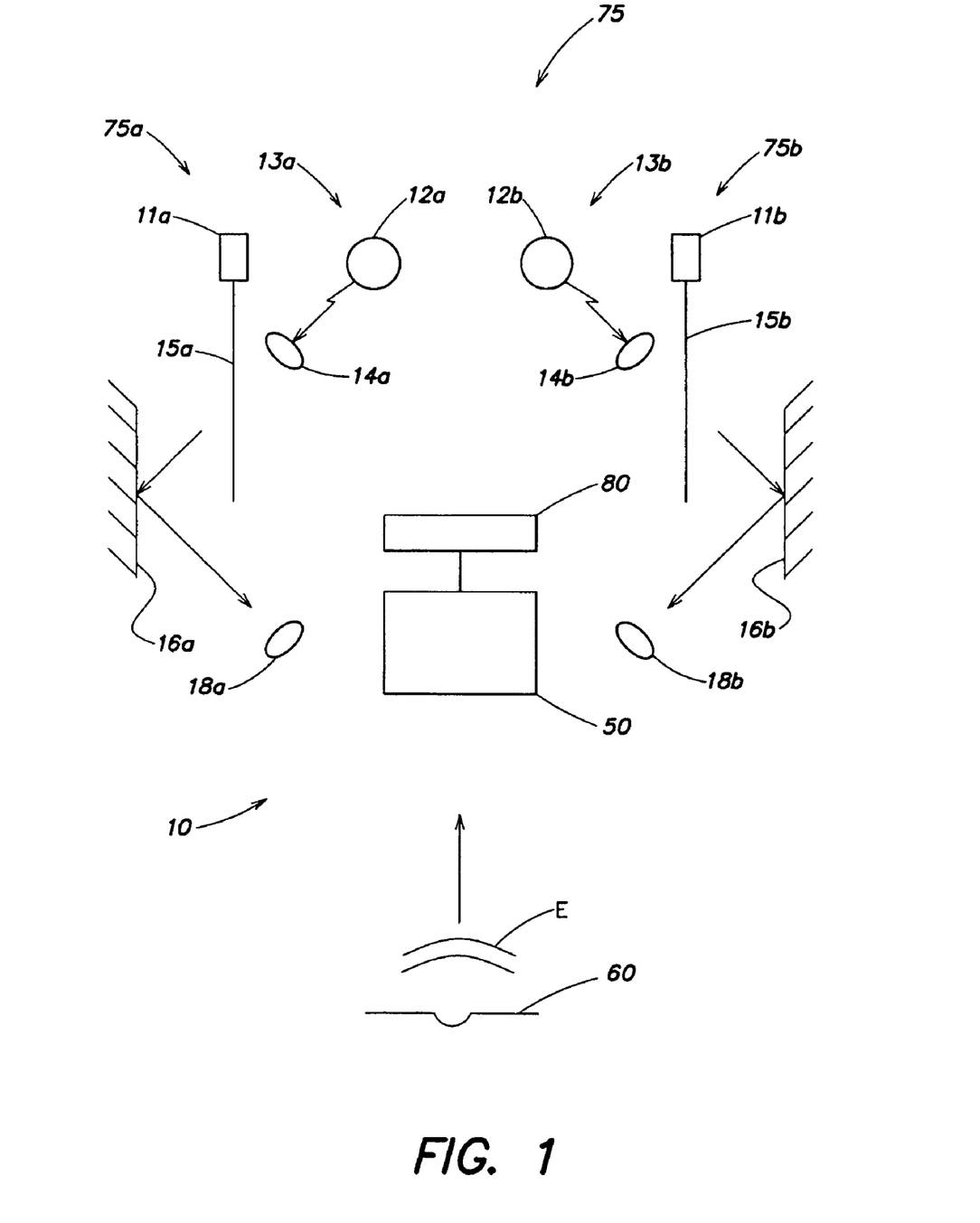
FIG. 1 is a schematic view of an example of a corneal measurement apparatus according to aspects of the present invention.

FIG. 1 is a schematic illustration of one example of a measurement apparatus 10 for facilitating elimination of ambient light from an image of an object (e.g., eye E). The apparatus comprises an illumination apparatus 75 (comprising a left arm 75a and a first arm 75b), an image sensor 50 and a processor 80.

Illumination apparatus 75 is adapted to sequentially illuminate the object using multiple lighting arrangements, including a first lighting arrangement and a second lighting arrangement. The illumination apparatus comprises two slit projection systems 13a, 13b (including light sources 12a and 12b, respectively) and slit masks 15a, 15b. Masks 15a and 15b are disposed in the paths of light from slit projection systems 13a and 13b, respectively.

Slit projection system 13a and mask 15a are in a left arm 75a of the corneal measurement apparatus, and slit projection system 13b and mask 15b are in a right arm 75b of the corneal measurement apparatus. In the illustrated embodiment, the left arm projects slits of light onto one half of the cornea, and the first arm projects slits of light onto the other half of the cornea. For example, the path of each of the projected slits of light may be at an approximately forty-five degree angle to the visual axis of the subject's eye.

In the illustrated embodiment, light arrangements are achieved by selectively illuminating sources 12a and 12b and positioning slit masks 15a and 15b using motors 11a and 11b. The masks are positioned such that the first light arrangement and the second lighting arrangement are known (i.e., predetermined).

In FIG. 1, condenser lenses 14a, 14b gather light from sources 12a and 12b respectively, and projector lenses 18a, 18b are configured and arranged such that the condenser lenses images sources 12a and 12b onto the projector lenses 18a, 18b, respectively. Although the illustrated embodiment of a measurement apparatus has two arms, in other embodiments, a measurement apparatus may have one or more arms.

Image sensor 50 may comprise any suitable image sensor, such as a CCD or a CMOS sensor. Additionally, one or more imaging optical components (e.g., lenses or mirrors) (not shown) may be present to gather light for image formation.

Apparatus 10 is adapted to form on the images sensor multiple images, each obtained using a different illumination arrangement, including (i) a first image of an object using a first illumination arrangement (e.g., a slit of light is projected using left slit projection system 13a), (ii) a second image of the object using the second illumination arrangement (e.g., a slit of light is projected using right slit projection system 13b), and (iii) a dark image of the object without slit illumination. The dark image is captured when no slits are illuminated; however, it will be appreciated that ambient illumination may be present in the dark image. For example, the ambient illumination may be from room lighting or a measurement apparatus light source other than a slit projector (e.g., illumination from an eye tracker). Aspects of the present invention are directed to identification and elimination of the effects of ambient illumination from images obtained by image sensor 50.

Processor 80 is operatively coupled to the image sensor and is programmed to reduce of eliminate ambient illumination. As described in greater detail below, processor is adapted: A) to compare an intensity value of a pixel in the first image to an intensity value of a corresponding pixel in the second image to determine a minimum intensity value, B) to determine if the minimum intensity value is greater than an intensity value of a corresponding pixel in the dark image by greater than a predetermined amount; and C) to identify an ambient intensity value (a) as the minimum intensity value, if the minimum intensity value is not greater than the intensity value of the pixel in the dark image by greater than the predetermined amount, or (b) as the intensity value of the pixel in the dark image, if the minimum intensity value is greater than the intensity value of the pixel in the dark image by greater than the predetermined amount. The term "corresponding pixels" or "corresponding portions" refers to portions of the images containing sub-images of a common feature of the object. For example, the predetermined amount may be equal to a selected number of gray scale levels.

The process of comparing intensity values of corresponding pixels in the first and second images can be repeated for one or more additional sets of corresponding pixels in the images. The step of comparing corresponding can be performed for each of the pixels of the first and second images or a subset of pixels of the first image and/or the second image. The predetermined amount used in the determination of element B) can be the same for all sets of pixels of can vary.

A measurement apparatus as shown in FIG. 1 typically obtains images of the eye as it is illuminated by slits projected onto tens of different locations on the eye (i.e., tens of cross sections are obtained). It will also be appreciated that the first image and the second image may constitute a subset of multiple images. Each image results in an image of a cross section of a selected portion of the eye. It will be appreciated that the information in the images (before or after ambient illumination reduction) can be combined to produce a two-dimensional or a three-dimensional representation of the eye using conventional techniques. According to aspects of the present invention, the processor is adapted to combine cross sectional images to achieve a two-dimensional or three-dimensional representation of an eye, and at least one cross sectional image has had its ambient illumination reduced in accordance with the techniques described herein.

Corneal measurement apparatus 10 includes a subject positioning apparatus 60 adapted to maintain a subject's cornea in a location. For example, the apparatus may be provided with a chin rest and/or a forehead rest which will fix the location of the subject's head during image acquisition.

Figure 2:
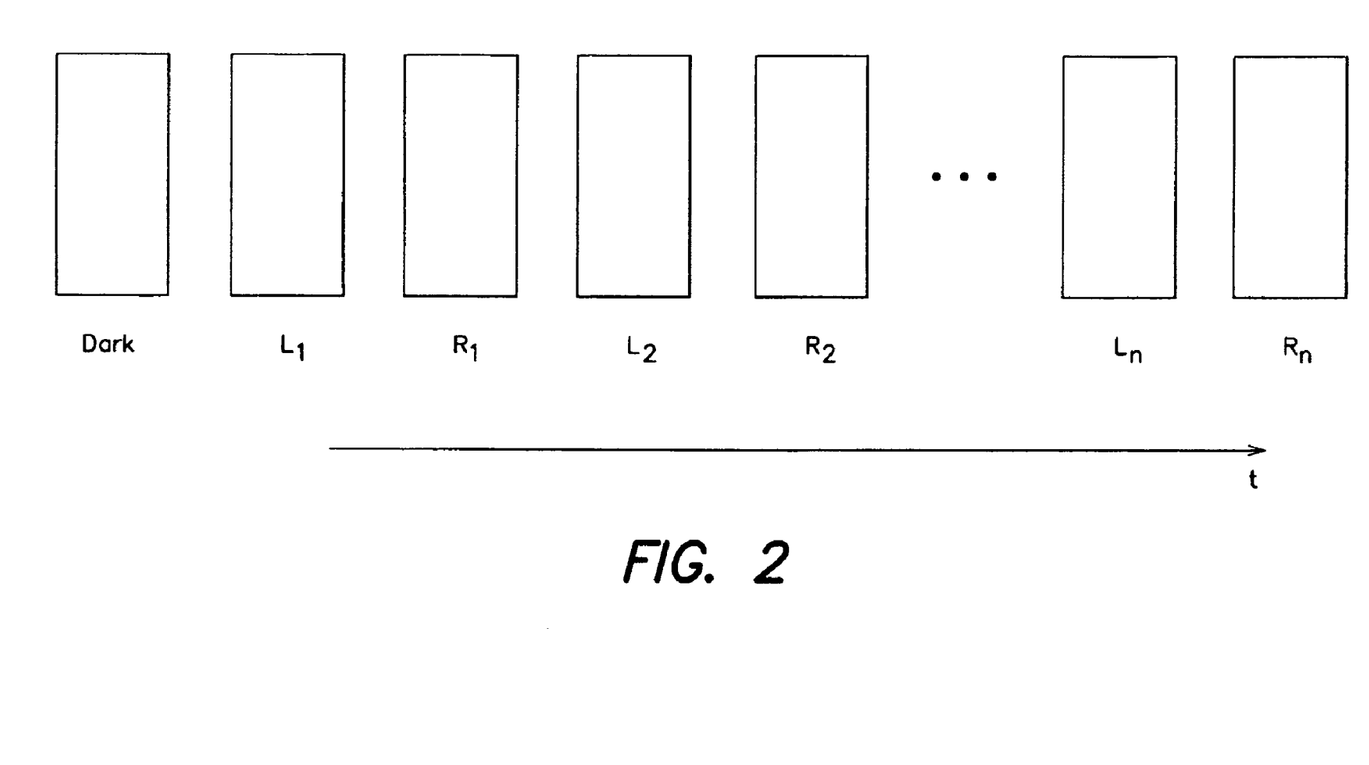
FIG. 2 is a schematic representation of images obtained sequentially by apparatus of FIG. 1.

As shown in FIG. 2, the multiple images are obtained sequentially. In the illustrated embodiment, images obtained with slit illumination from the left arm are designated with an L, and images obtained with illumination from the right arm are designated with an R. Increasing time is indicated by the letter "t". All of the images are typically obtained in less than one second; however, any suitable time period may be used for image acquisition. First and second images as described above are preferably obtained in a short interval of time to avoid the effects of eye movement. If the eye does not move a substantial amount, a same pixel (a pixel at a given row and column of the sensor elements) in each of the first and second images can be compared without any further analysis to determine if they are sub-images of a common feature of the object. However, images to be compared can be translated, rotated or otherwise aligned to one another prior to comparison.

In some embodiments, it is advantageous if the first and second images are two successive images to minimize the interval of time between the images; however such a selection of the images is not necessary.

The dark image can be obtained at any suitable time within time interval T. However, obtaining a dark image before or after acquisition of the other images typically reduces the time interval that occurs between slit images to be compared. Although, in the description above, a minimum was determined using two images, three or more images may be used to determine the minimum.

In some embodiments, sensor 50 is an interlaced video imager. In such embodiments, the first and second images may be successive images. It will be appreciated that, in some embodiments having interlaced images, the pixels in the first image will not spatially correspond to pixels in the second image to a desired degree. Interpolation of columns of pixels in one of the images can be performed along the direction of interlacing so that intensity values of corresponding locations can be obtained prior to comparison and determination of the minimum values.

Figure 3A:
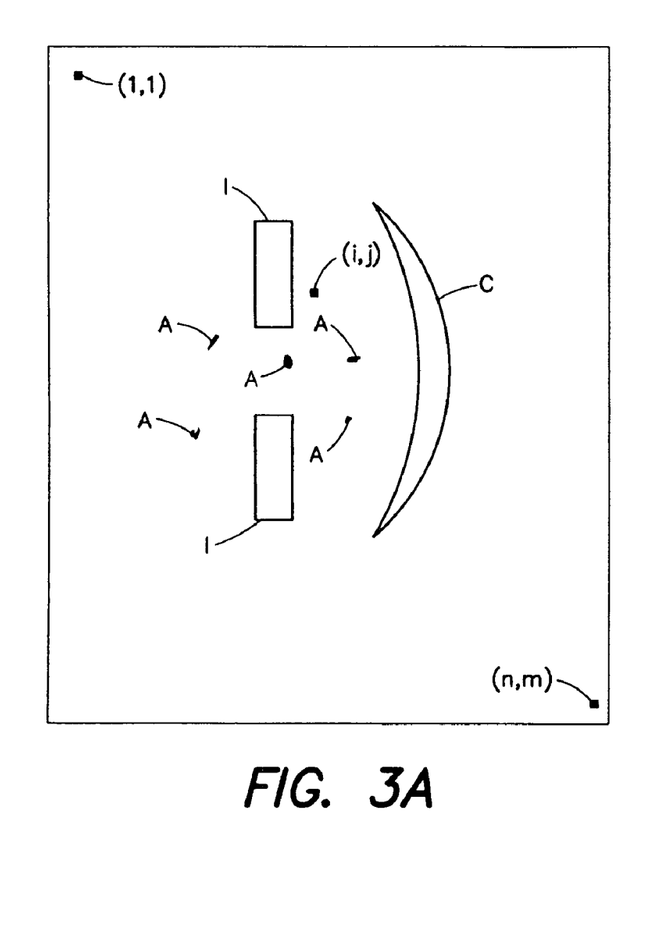
FIG. 3A is a schematic representation of a first image taken with slit illumination from a left illumination arm of the apparatus of FIG. 1.
Figure 3B:
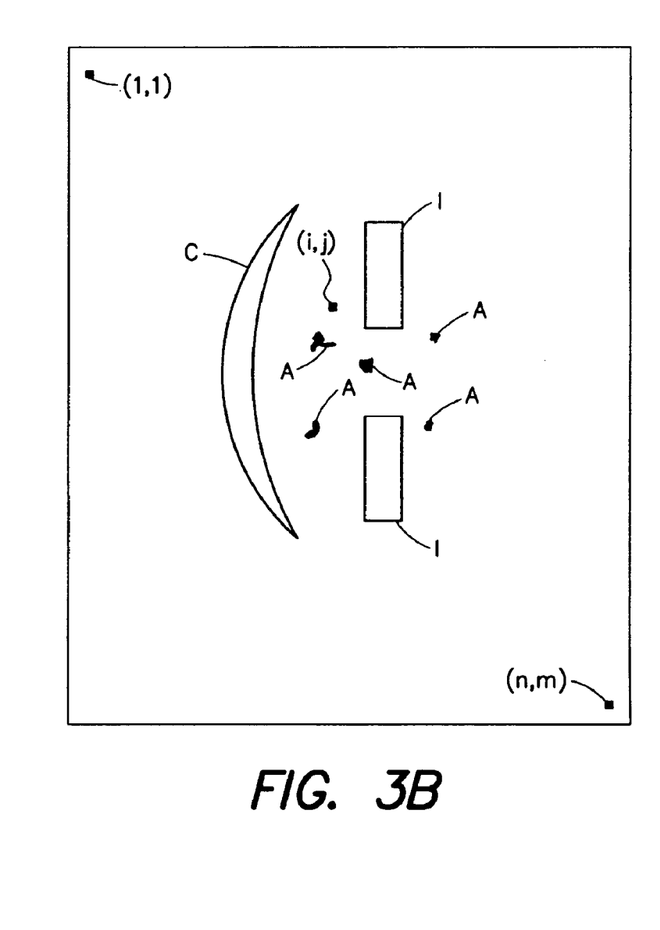
FIG. 3B illustrates a schematic representation of a second image taken with slit illumination from a right illumination arm of the apparatus of FIG. 1.
Figure 3C:
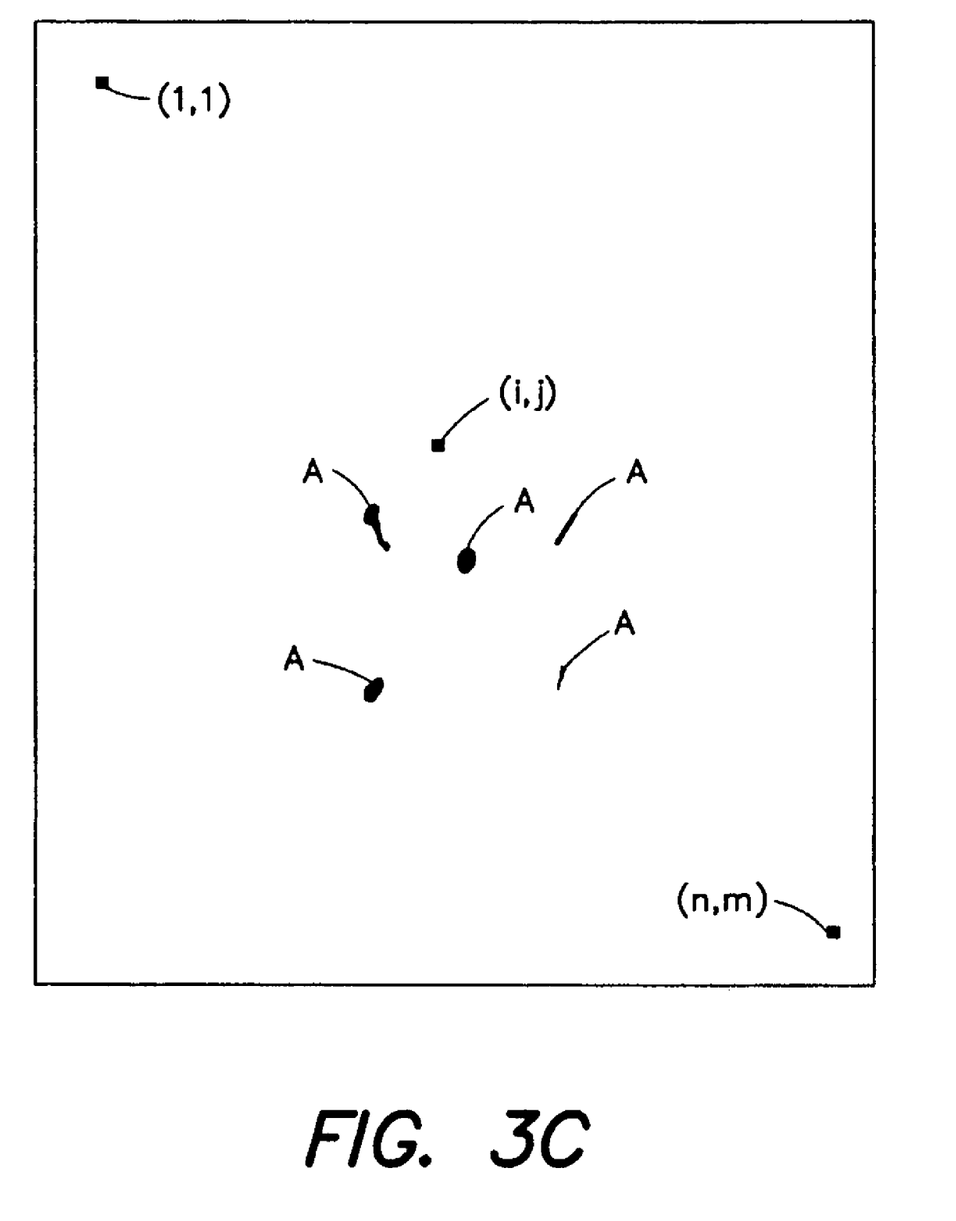
FIG. 3C illustrates a schematic representation of a dark image obtained by the apparatus of FIG. 1 that was taken with no slit illumination.

FIG. 3A illustrates a first image taken with slit illumination from left arm 75a (shown in FIG. 1). FIG. 3B illustrates a second image taken with slit illumination from right arm 75b (shown in FIG. 1). FIG. 3C illustrates a dark image taken with no slit illumination. Each of images 3A-3C shows a cross section of eye E and representative pixels (1,1), (i,j) and (n,m) of sensor 50. Each of FIGS. 3A and 3B show an image of slit light scattered from the cornea C and the iris I, as well as light other than the slit light that is scattered or reflected from features of the eye. Light other than scattered slit light is labeled A for ambient.

Figure 4:
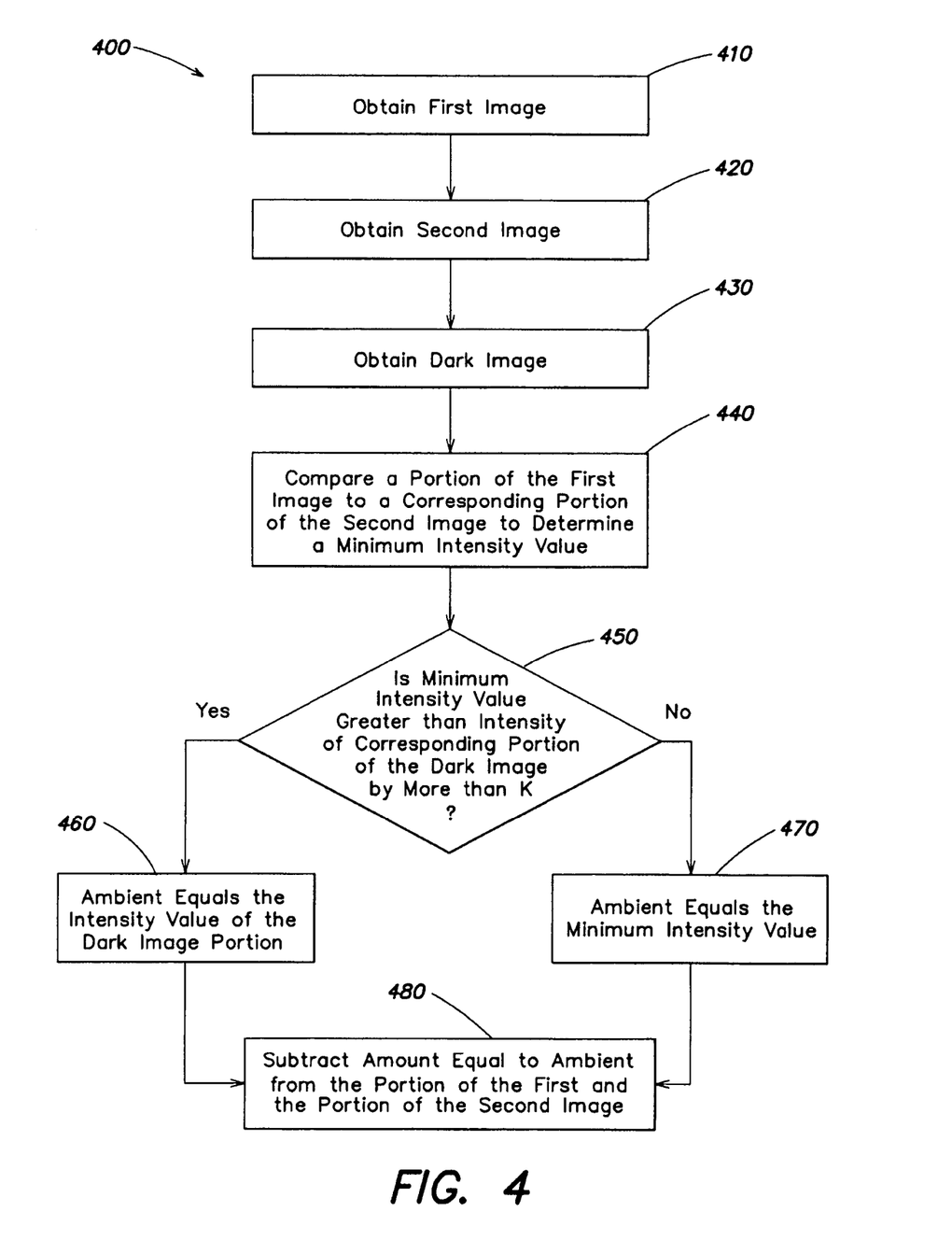
FIG. 4 is a flow chart illustrating an example of a method according to aspects of the present invention.

FIG. 4 is a flow chart illustrating an embodiment of a method 400 to reduce the effects of ambient illumination according to aspects of the present invention. At step 410, a first image of an object using a first illumination arrangement is obtained. Capture of the first image was described in greater detail above.

At step 420, a second image of the object using a second illumination arrangement is obtained. Capture of the second image was described in greater detail above.

At step 430, a dark image without illumination. Capture of the dark image was described in greater detail above.

At step 440, an intensity value of a pixel (i,j) in the first image is compared to an intensity value of a corresponding pixel (i,j) in the second image to determine a minimum intensity value $I_{min}(i,j)$. Corresponding pixels refers to those pixels that image the same or substantially the same portion of an object (e.g., eye E). As described above, interpolation of an output of a sensor or other processing may be performed on images prior to comparison. It will be understood that as used herein the term "pixel" refers to a pixel (i.e., a portion) of the image. Pixels of an image may comprise one or more pixels of an image sensor.

At step 450, the minimum intensity value $I_{min}(i,j)$ is compared to an intensity value of a corresponding pixel in the dark image $I_{dark}(i,j)$. At step, it is determined whether the minimum intensity value $I_{min}(i,j)$ is greater than an intensity value of the pixel in the dark image by greater than a predetermined amount K.

$$I_{min}(i,j) < I_{dark}(i,j) + K$$

An ambient intensity value A(i,j) is identified (1) as the minimum intensity value, if the minimum intensity value is not greater than the intensity value of the pixel in the dark image by greater than the predetermined amount (step 460), or (2) as the intensity value of the pixel in the dark image, if the minimum intensity value is greater than the intensity value of the pixel in the dark image by greater than the predetermined amount (step 470).

At step 480, an intensity value equal to the ambient intensity value A(i,j) is subtracted from one or both of the pixel (i,j) in the first image and the pixel (i,j) in the second image. It will be appreciated that if a minimum was determined using three images, a value equal to the ambient intensity may be subtracted from corresponding pixels in all three images. The method may be repeated for all portions (e.g., pixels) of the first and second images or only a subset of all of the portions.

Steps 450 through 470, are included because, in some instances, one or more of the images may include a portion of the eye illuminated by a slit of light in the portion (e.g., pixel) at which a comparison takes place. As stated above, it will be appreciated that, if only one image includes the image of the slit, the method will accurately identify the minimum value as an indication of the amount of ambient light present at that portion. However, if both images include a portion of the eye illuminated by a slit of light, the minimum will not be indicative of the ambient illumination.

Accordingly, after a minimum value is determined for a particular portion of the eye, the minimum is compared to a portion of the dark image showing a corresponding portion of the eye. If the minimum intensity value is greater than the intensity value of the pixel in the dark image by greater than a predetermined amount, it is assumed that the minimum as determined using the first and second images corresponds to a portion of the eye illuminated by a slit of light, and the amount of ambient light present at the portion is taken as the value present in the corresponding portion of the dark image.

It will be appreciated that, while it would be possible to obtain a dark image to determine the ambient for each set of images for which a minimum is calculated, acquisition of such dark images is time consuming and may be undesirable. According to aspects of the present invention, the number of dark images is less than the number of sets of slit images for which a minimum is determined (i.e., a dark image is not obtained for each set of slit images); and in some embodiments, only a single dark image is obtained for all of the slit images that are used to generate a two-dimension or three-dimension representation of an eye. It will be appreciated that, by reducing the number of dark images obtained, the time for acquiring data can be reduced. It will also be appreciated that, despite reducing the number of dark images that are obtained, accuracy of the amount of ambient light at any given portion can be maintained by using information from the dark image only in the event that the minimum amount of light deviates from the amount of light in the dark image by a substantial amount.

Figure 5:
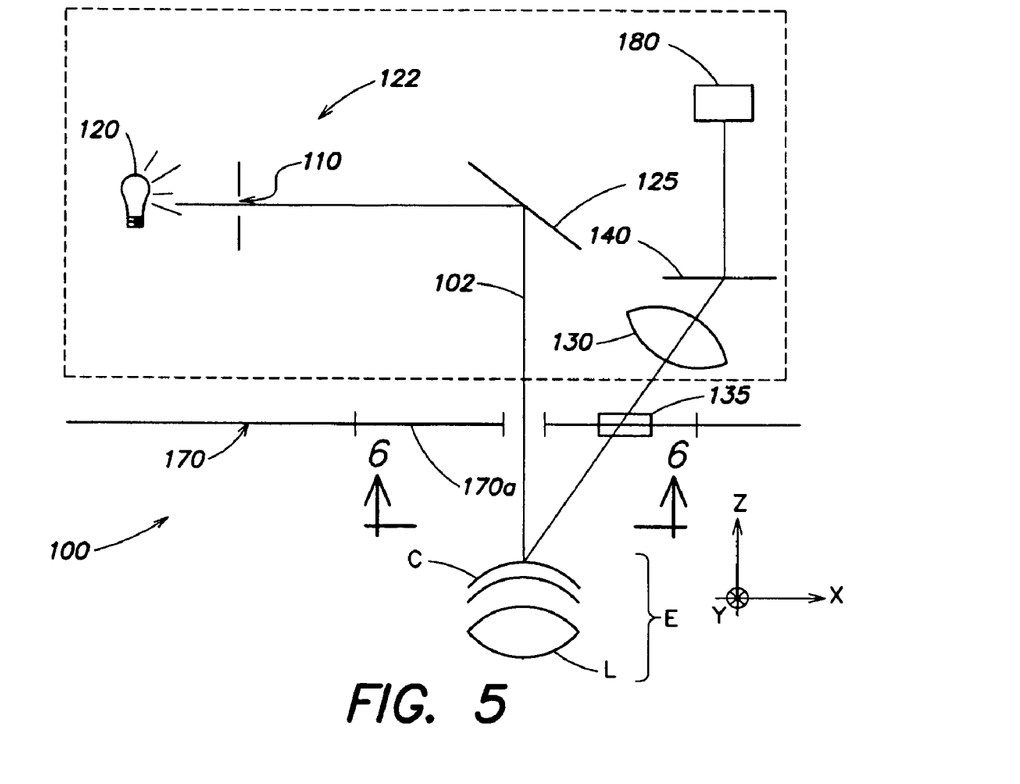
FIG. 5 illustrates another example of an embodiment of a measurement apparatus in which a first light arrangement S and second light arrangement S' are achieved by projecting slits at various angular deviations (a) about an instrument axis.
Figure 6:
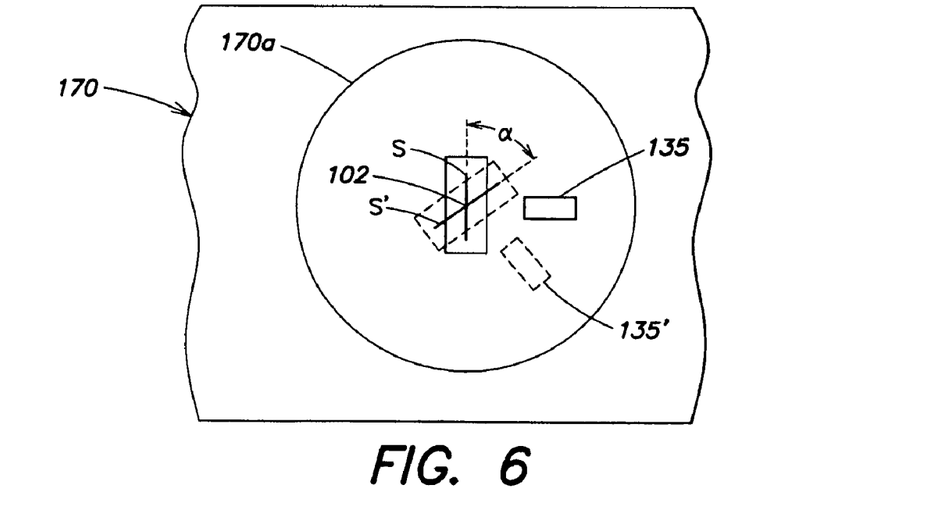
FIG. 6 is a view of apparatus taken along line 6-6 of FIG. 5.

FIGS. 5 and 6 illustrate another example of an embodiment of a measurement apparatus 100 in which a first light arrangement S and second light arrangement S' are achieved by projecting slits at various angular deviations (a) about an instrument axis 102, and are thereby projected such that the slits impinge on multiple locations on the cornea C. FIG. 6 is a view of apparatus 100 taken along line 6-6 of FIG. 5. Light scattered by the eye from each slit permits a cross section of the eye to be obtained; and multiple cross sections from slits of different angular deviations permit two-dimensional or three-dimensional representations of the eye to be constructed as was described above.

To produce slits of light S, S', the apparatus includes a slit projector 122 comprising a long, thin aperture 110 (having a length extending in the Y direction in FIG. 5) placed in front of a source 120. A beam splitter or mirror 125 reflects the slits of light along an instrument axis 102 onto an eye having a cornea C and lens L. To achieve slits of light S and S' at the various angular deviations, apparatus 100 (including all components therein) and a portion 170a of the front faceplate 170 of the apparatus is rotated about instrument axis 102. After the light is scattered by the eye, the scattered light re-enters the apparatus through a camera port 135 and is gathered by lens 130 and projected onto an image sensor 140. Port 135 is positioned as indicated by reference number 135' when capturing light from slit S'. One image is obtained for each of a plurality of rotational positions of the apparatus.

As with apparatus described above with reference to FIGS. 1 and 2, the apparatus is adapted to form on images sensor 140 (i) a first image of an object (e.g., eye E) using a first illumination arrangement (e.g., a slit of light S is projected), (ii) a second image of the object using the second illumination arrangement (e.g., a slit of light S' is projected), and (iii) a dark image of the object without illumination. That is to say the dark image is captured when no slits are illuminated; however, ambient illumination (which is to be eliminated) may be present in the dark image.

As described in greater detail below, a processor 180 is adapted to A) compare an intensity value of pixel in the first image to an intensity value of a corresponding pixel in the second image to a determine a minimum intensity value, B) compare the minimum intensity value to an intensity value of a corresponding pixel in the dark image. However, it will be appreciated that since sensor 140 is moved relative to the object (e.g., eye E) to obtain the first image and second image, and possibly the dark image, it is typically desirable to perform a perspective transform on one or more of the first, second and dark images prior to comparison of portions of the eye so that the images correspond to a common perspective. The perspective transform may be achieved, for example, as described in U.S. patent application Ser. No. 12/264,965, titled EYE MEASUREMENT APPARATUS AND METHODS OF USING SAME, filed Nov. 5, 2008, by Allred, et al. The substance of said application is hereby incorporated by reference.

Similar to the apparatus described above, processor 180 is operatively coupled to sensor 140 and is adapted to C) determine if the minimum intensity value is greater than the intensity value of the pixel in the dark image by greater than a predetermined amount; and D) identify an ambient intensity value (a) as the minimum intensity value, if the minimum intensity value is not greater than the intensity value of the pixel in the dark image by greater than the predetermined amount, or (b) as the intensity value of the pixel in the dark image, if the minimum intensity value is greater than the intensity value of the pixel in the dark image by greater than the predetermined amount.

Having thus described the inventive concepts and a number of exemplary embodiments, it will be apparent to those skilled in the art that the invention may be implemented in various ways, and that modifications and improvements will readily occur to such persons. Thus, the embodiments are not intended to be limiting and presented by way of example only. The invention is limited only as required by the following claims and equivalents thereto.

What is claimed is:

1. A method of facilitating elimination of ambient light from an image, comprising:
   A) obtaining a first image of an object using a first illumination arrangement;
   B) obtaining a second image of the object using a second illumination arrangement;
   C) obtaining a dark image without illumination;
   D) comparing an intensity value of a first pixel in the first image to an intensity value of a corresponding, first pixel in the second image to determine a first minimum intensity value;
   E) determining if the first minimum intensity value is greater than an intensity value of a corresponding, first pixel in the dark image by greater than a predetermined amount; and
   F) identifying an ambient intensity value (a) as the first minimum intensity value, if the first minimum intensity value is not greater than the intensity value of the first pixel in the dark image by greater than the predetermined amount, or (b) as the intensity value of the first pixel in the dark image, if the first minimum intensity value is greater than the intensity value of the first pixel in the dark image by greater than the predetermined amount;
   G) subtracting an intensity value equal to the ambient intensity value from one or both of the first pixel in the first image and the first pixel in the second image;
   H) comparing an intensity value of a second pixel in the first image to an intensity value of a corresponding, second pixel in the second image to determine a second minimum intensity value;
   I) determining if the second minimum intensity value is greater than an intensity value of a corresponding, second pixel in the dark image by greater than a second predetermined amount; and
   J) identifying an ambient intensity value (a) as the second minimum intensity value, if the second minimum intensity value is not greater than the intensity value of the second pixel in the dark image by greater than the predetermined amount, or (b) as the intensity value of the second pixel in the dark image, if the second minimum intensity value is greater than the intensity value of the second pixel in the dark image by greater than a second predetermined amount.

2. The method of claim 1, wherein the first illumination arrangement is achieved using a first slit arrangement and the second illumination arrangement is achieved using a second slit arrangement.

3. The method of claim 2, wherein the first illumination arrangement and the second illumination arrangement are achieved by selectively illuminating multiple slit projectors.

4. The method of claim 2, wherein the first illumination arrangement and the second illumination arrangement are achieved by selectively positioning one or more slit masks.

5. The method of claim 4, wherein the selective positioning comprises at least one of translation and rotation of the one or more slit masks.

6. The method of claim 1, wherein the first image and the second image constitute two images of a plurality of images of an eye, the method further comprising combining the plurality of images of the eye to produce a two-dimensional or a three-dimensional representation of the eye.

7. The method of claim 1, further comprising a step of performing a perspective transform on at least one of the first image and the second image prior to step D).

8. An apparatus for facilitating elimination of ambient light from an image of an object, comprising:
   an illumination apparatus adapted to sequentially illuminate the object using a first lighting arrangement and a second lighting arrangement;

an image sensor, the apparatus adapted to form on the image sensor (i) a first image of the object using the first illumination arrangement, (ii) a second image of the object using the second illumination arrangement, and (iii) a dark image of the object without illumination; and
a processor coupled to the image sensor adapted to—
A) compare an intensity value of a first pixel in the first image to an intensity value of a corresponding, first pixel in the second image to determine a first minimum intensity value,
B) determine if the first minimum intensity value is greater than an intensity value of a corresponding, first pixel in the dark image by greater than a predetermined amount; and
C) identify an ambient intensity value (a) as the first minimum intensity value, if the first minimum intensity value is not greater than the intensity value of the first pixel in the dark image by greater than the predetermined amount, or (b) as the intensity value of the first pixel in the dark image, if the first minimum intensity value is greater than the intensity value of the first pixel in the dark image by greater than the predetermined amount
D) compare an intensity value of a second pixel in the first image to an intensity value of a corresponding, second pixel in the second image to determine a second minimum intensity value,
E) determine if the second minimum intensity value is greater than an intensity value of a corresponding, second pixel in the dark image by greater than a second predetermined amount; and
F) identify an ambient intensity value (a) as the second minimum intensity value, if the second minimum intensity value is not greater than the intensity value of the second pixel in the dark image by greater than the second predetermined amount, or (b) as the intensity value of the second pixel in the dark image, if the second minimum intensity value is greater than the intensity value of the second pixel in the dark image by greater than the second predetermined amount.

9. The apparatus of claim 8, wherein the illumination apparatus comprises one or more slit masks configured to achieve the first illumination arrangement and the second illumination arrangement.

10. The apparatus of claim 8, wherein the illumination apparatus comprises a plurality of slit projectors adapted to be selectively illuminated to achieve the first slit arrangement and the second slit arrangement.

11. The apparatus of claim 8, wherein the illumination apparatus comprises one or more slit projectors adapted to be selectively positioned to achieve the first slit arrangement and the second slit arrangement.

12. The apparatus of claim 11, wherein the one or more slit projectors are adapted to be translated to achieve the first slit arrangement and the second slit arrangement.

13. The apparatus of claim 11, wherein the one or more slit projectors are adapted to be rotated to achieve the first slit arrangement and the second slit arrangement.

14. The apparatus of claim 11, wherein the processor is adapted to subtract an intensity value equal to the ambient intensity value from one or both of the first pixel in the first image and the first pixel in the second image.

15. The apparatus of claim 11, wherein the apparatus is adapted to obtain a plurality of images of an eye, the first image and the second image constituting two images of the plurality of images, and wherein the processor is adapted to combine the plurality of images of the eye to produce a two-dimensional or a three-dimensional representation of the eye.

16. The apparatus of claim 11, wherein the processor is adapted to perform a perspective transform on at least one of the first image and the second image prior to the comparing of the intensity value of the first pixel in the first image to the intensity value of the corresponding, first pixel in the second image to determine the first minimum intensity value.

17. The apparatus of claim 8, wherein the processor is adapted to interpolate intensity values in the first image prior to comparison of an intensity value of the pixel in the first image to the intensity value of the corresponding, first pixel in the second image to determine the first minimum intensity value.

18. The apparatus of claim 17, wherein the image sensor is an interlaced image sensor and the first image and the second image constitute interlaced images.

* * * * *